US009155547B2

(12) United States Patent
Torrie et al.

(10) Patent No.: US 9,155,547 B2
(45) Date of Patent: Oct. 13, 2015

(54) ARTHROSCOPIC JOINT REPAIR

(75) Inventors: Paul Alexander Torrie, Marblehead, MA (US); Marc J Philippon, Edwards, CO (US)

(73) Assignee: Smith & Nephew, Inc., Memphis, TN (US)

( * ) Notice: Subject to any disclaimer, the term of this patent is extended or adjusted under 35 U.S.C. 154(b) by 76 days.

(21) Appl. No.: 13/288,934

(22) Filed: Nov. 3, 2011

(65) Prior Publication Data

US 2012/0116408 A1 May 10, 2012

Related U.S. Application Data

(60) Provisional application No. 61/410,078, filed on Nov. 4, 2010.

(51) Int. Cl.
*A61B 17/17* (2006.01)
*A61B 17/00* (2006.01)

(52) U.S. Cl.
CPC ..... *A61B 17/1746* (2013.01); *A61B 2017/0046* (2013.01)

(58) Field of Classification Search
CPC .................................................. A61B 17/1746
USPC ................................ 606/81, 91, 96–98, 86 R
See application file for complete search history.

(56) References Cited

U.S. PATENT DOCUMENTS

| | | | | |
|---|---|---|---|---|
| 5,601,550 | A | 2/1997 | Esser | |
| 2003/0009173 | A1 | 1/2003 | McGuire et al. | |
| 2006/0106398 | A1 | 5/2006 | Lauryssen et al. | |
| 2007/0191853 | A1 | 8/2007 | Stone | |
| 2009/0069845 | A1* | 3/2009 | Frushell et al. | 606/228 |
| 2010/0016984 | A1 | 1/2010 | Trabish | |
| 2010/0268241 | A1* | 10/2010 | Flom et al. | 606/104 |
| 2012/0046526 | A1* | 2/2012 | Boettner et al. | 600/210 |

FOREIGN PATENT DOCUMENTS

FR 2906452 A1 4/2008

OTHER PUBLICATIONS

International search report and written opinion regarding International patent application PCT/US2011/059242 mailed on Mar. 26, 2012.
International search report regarding International patent application PCT/US2011/059242 mailed on Feb. 10, 2012.
Communication pursuant to Article 94(3) EPC mailed Apr. 10, 2014.
Communication pursuant to Article 94(3) EPC for EP Application No. 11781974.8, mailed May 27, 2015.

* cited by examiner

*Primary Examiner* — Samuel Hanna
(74) *Attorney, Agent, or Firm* — Burns & Levinson LLP; Joseph M. Maraia

(57) ABSTRACT

The present disclosure relates to a guide. The guide includes a handle and a shaft coupled to the handle, the shaft including a lip located at a distance from the longitudinal axis of the shaft and extending a distance from an end of the shaft. A method of tissue repair is also disclosed.

16 Claims, 3 Drawing Sheets

ARTHROSCOPIC JOINT REPAIR

CROSS-REFERENCE TO RELATED APPLICATIONS

This application claims priority to U.S. Patent Application Ser. No. 61/410,078, the disclosure of which is incorporated herein in its entirety.

BACKGROUND

1. Field of Technology

The present disclosure relates generally to arthroscopic soft tissue repair and, in particular, arthroscopic labral repair in the hip joint.

2. Related Art

As shown in FIG. 1, the acetabular labrum 11 is a ring of soft tissue that encircles the acetabulum 10 near the entrance to the acetabular cup or socket 12. In some cases, the labrum 11 is torn off of the acetabulum 10, or acetabular rim 13, and needs to be reattached. Currently, fixation devices, such as suture anchors, are used to reattach the labrum 11 to the acetabulum 10. However, due to complications in visualization of the area of anchor placement, placement of the suture anchor is done blind or without the surgeon being able to see where the anchor is being placed. As shown in FIG. 2, there is a risk that the anchor, or anchor hole 14, may be placed with an incorrect trajectory such that the possibility of it breaking into the articular cartilage 15 of the socket 12 is increased. Not only could this cause damage to the cartilage 15, but it could also lead to damage to the femoral head (not shown), which is housed within the socket 12.

As shown in FIG. 3, in order to avoid damaging the cartilage 15 and femoral head, the anchor hole 14 is placed in a location that is a certain distance X from the acetabular cartilage 15 surface. When the labrum 11 is reattached via use of the anchor 16 and suture 17, the labrum 11 is positioned in a non-anatomic location or off of the rim 13, as shown in FIG. 3. Having the labrum 11 positioned in a non-anatomic location may lead to further problems with the hip joint, specifically the labrum 11 will not be able to perform its primary role of creating a seal against the head of the femur. Therefore, a method and instrument for use therewith that would precisely position the anchor 16 relative to the acetabular cartilage surface 15 is needed.

SUMMARY

In an aspect, the present disclosure relates to a guide. The guide includes a handle and a shaft coupled to the handle, the shaft including a lip located at a distance from the longitudinal axis of the shaft and extending a distance from an end of the shaft.

In an embodiment, the shaft includes a proximal end and a distal end, the handle is coupled to the proximal end. In another embodiment, the lip extends from the distal end of the shaft. In yet another embodiment, the shaft and the handle are cannulated. In a further embodiment, the distance the lip is located from the longitudinal axis of the shaft is about 1 mm to about 5 mm. In yet a further embodiment, the distance the lip extends from the end of the shaft is about 13 mm to about 25 mm. In an embodiment, the guide further includes a slidable tube. In another embodiment, the tube is located within a cannulation of the shaft. In yet another embodiment, the tube is configured to extend from an end of the shaft. In a further embodiment, the guide further includes a movable jaw. In yet a further embodiment, the movable jaw is located at an end of the shaft. In an embodiment, the movable jaw includes teeth. In another embodiment, the guide further comprises an arthroscope.

In another aspect, the present disclosure relates to a method of tissue repair. The method includes providing a guide, the guide comprising a handle and a shaft coupled to the handle, the shaft including a lip located at a distance from a longitudinal axis of the shaft and extending a distance from an end of the shaft; introducing the guide into a hip joint such that the lip engages a surface of an acetabulum socket; delivering an anchor into the acetabulum via use of the guide; and using the anchor to reattach a labrum to the acetabulum.

In an embodiment, the method further comprises creating a hole in the acetabulum via use of the guide. In another embodiment, the guide further includes a slidable tube, an end of the tube configured for engagement with the acetabulum. In yet another embodiment, the guide further includes a movable jaw wherein the jaw is configured for engagement with the acetabulum. In a further embodiment, the guide further includes an arthroscope. In yet a further embodiment, the distance the lip is located from the longitudinal axis of the shaft is about 1 mm to about 5 mm. In an embodiment, the distance the lip extends from the end of the shaft is about 13 mm to about 25 mm.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION OF THE EMBODIMENTS

The following description of the preferred embodiment(s) is merely exemplary in nature and is in no way intended to limit the disclosure, its application, or uses.

Figure 1:
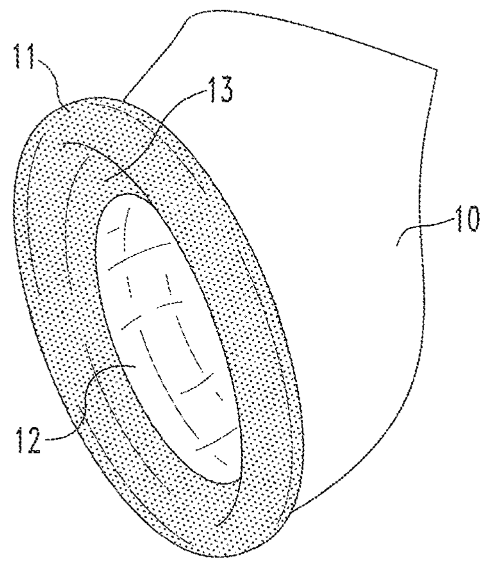
FIG. 1 shows a perspective view of the acetabulum and labrum.
Figure 2:
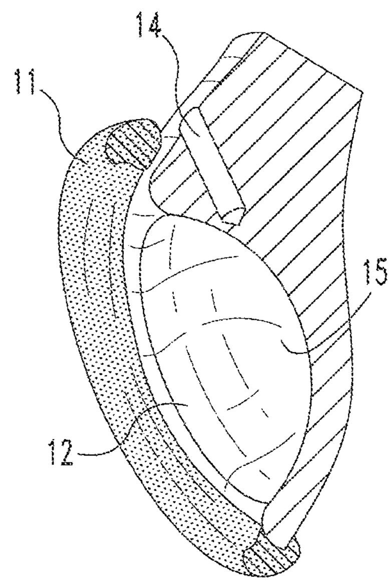
FIG. 2 shows a cross sectional view of the acetabulum and labrum with an anchor hole in the acetabulum.
Figure 3:
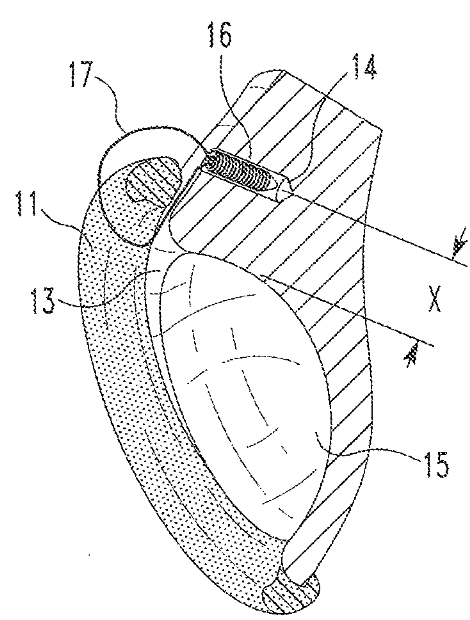
FIG. 3 also shows a cross-section view of the acetabulum and labrum with an anchor hole in the acetabulum.
Figure 4:
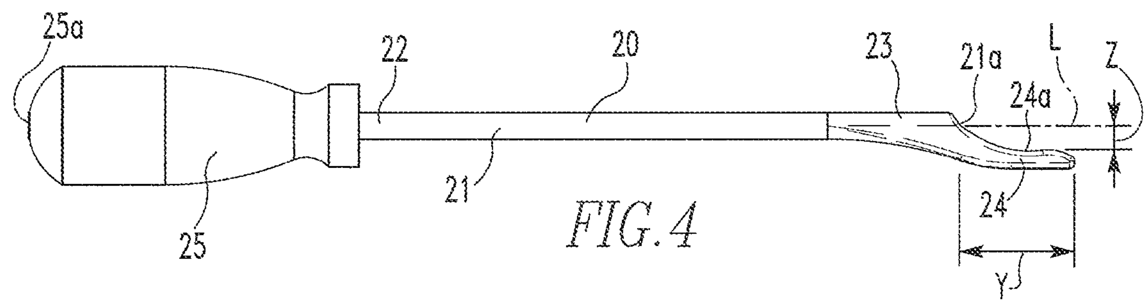
FIG. 4 shows a side view of a first guide of the present disclosure.

FIG. 4 shows a side view of the first guide 20 of the present disclosure. The guide 20 includes a shaft 21 having a proximal end 22 and a distal end 23. The distal end 23 includes a lip 24 having a surface **24*a* located a distance Z from the longitudinal axis L of the shaft 21. The lip 24** is offset from the shaft 21 such that during use as minimum a distance between the anchor hole 14 and the acetabular cartilage 15 surface are formed, as will be further described below. The distance Z may be between about 1 mm and about 5 mm. The lip 24 extends from the distal end a distance Y, which may be between about 13 mm and about 25 mm. A handle 25 is coupled to the proximal end 22 of the shaft 21. Both the handle 25 and the shaft 21 are cannulated such that the cannulations 25*a*, 21*a* are in line with each other. The handle 25 may be coupled to the shaft 21 via a mechanical means, via the use of an adhesive, or any other means known to one of skill in the art. The lip 24 may be permanently or releasably coupled to the distal end 23. If it is permanently coupled, it may be coupled to the shaft 21 via the use of a mechanical or chemical means or it may be formed as part of the shaft 21 at the same time the shaft 21 is made. If it is releasably coupled, it may be coupled to the shaft 21 via the use of a mechanical means or other means known to one of skill in the art.

Additionally, for the purposes of this disclosure, the shaft 21 is formed from a metal material and via a method known to one of skill in the art. Although, material other than metal that would withstand the forces placed on the shaft 21 during surgery may be used. Similarly, the handle 25 is formed from a plastic material and via a method known to one of skill in the art, but may be formed from another material known to one of skill in the art.

Figure 5:
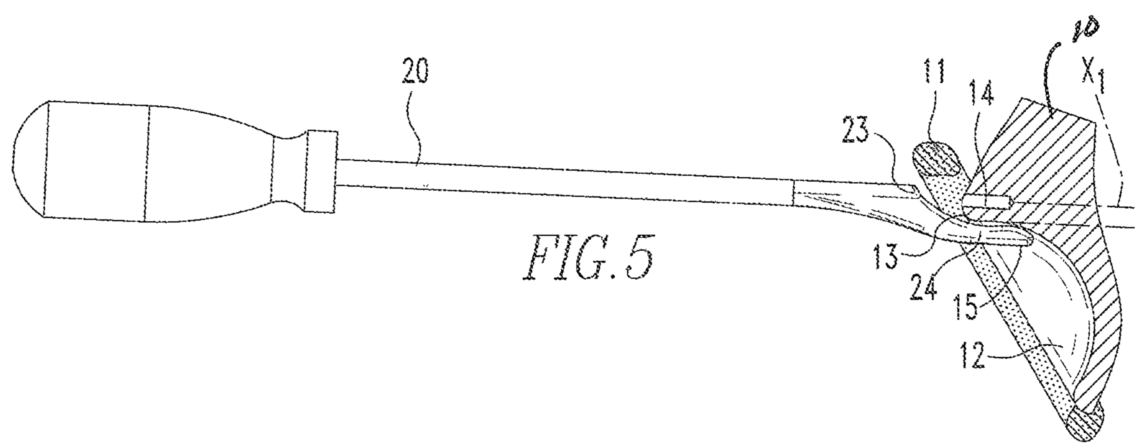
FIG. 5 shows a side view of the first guide of FIG. 4 during use in acetabular labral repair.

FIG. 5 shows the guide 20 in use during arthroscopic labral repair. The guide 20 is placed such that the lip 24 engages the cartilage 15 on the surface of the socket 12 next to the acetabular rim 13 and the distal end 23 is forced against the acetabulum 10. FIG. 5 does not show the distal end 23 as being forced against the acetabulum 10, but in practice engagement of the distal end 23 with the acetabulum 10 would occur. A drill (not shown) may then be placed through the guide 20 and operated to create a hole 14 for use with a suture anchor. It is within the scope of this disclosure that a device other than a drill may be used to create the hole 14. Alternatively, the suture anchor may be delivered into the acetabulum 10 via use of the guide 20 and an anchor delivery device (not shown) without first forming a hole in the acetabulum 10.

As stated above, the lip 24 is offset from the axis L of the shaft 21 such that as minimum a distance $X_1$ between the anchor hole 14 and the acetabular cartilage 15 surface are formed. This will substantially reduce the possibility of the labrum 11 being positioned in a non-anatomic location on the acetabulum 10 and, consequently, the problems that may stem therefrom, as described above. Additionally, the lip 24 may be contoured to distribute the pressure it exerts against the acetabular cartilage 15 so as to not damage the cartilage 15. Traditionally, the thick soft tissues (not shown) surrounding the hip joint and located below the shaft 21 have made changing the trajectory of the guide 20 somewhat difficult. By placing the lip 24 of guide 20 against the cartilage surface 15 next to the acetabular rim 13, the guide 20 is automatically angled into a useful trajectory and the amount of time spent trying to find the best trajectory is substantially reduced. Furthermore, the combination of the placement of the lip 24 and the engagement of at least a portion of the shaft 21 with the thick soft tissues surrounding the hip joint produces a lever such that the guide 20 is held stable within the joint.

Figure 6:
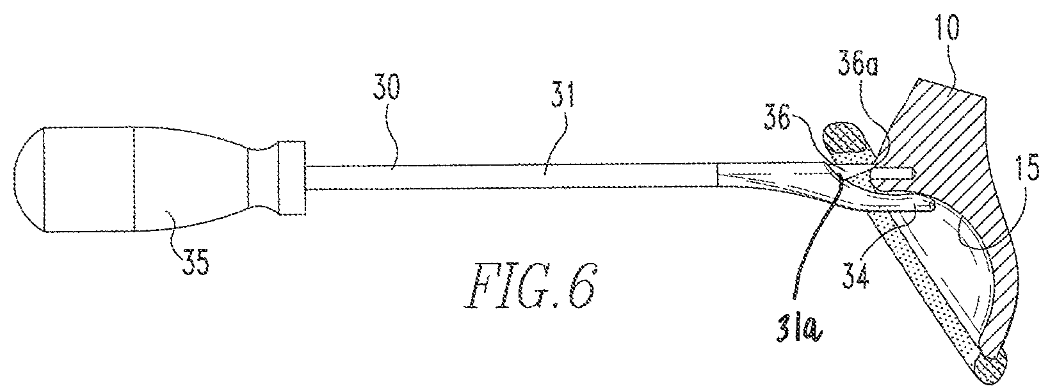
FIG. 6 shows a side view of a second guide of the present disclosure during use in acetabular labral repair.

FIG. 6 shows a second guide 30 for use in acetabular labral repair. The guide 30 is similar to guide 20 except guide 30 includes a slidable cannulated tube 36 located within the shaft 31. Specifically, the tube 36 is located within the cannulation 31*a* of the shaft 31. The tube 36 includes a distal end 36*a* shaped to engage the acetabulum 10, as will be further described below, and is movable along the length of the shaft 31 via the use of a lever (not shown) or other type of actuating mechanism coupled to a proximal end (not shown) of the tube 36. The lever may be located on the handle 35 or the shaft 31. During use, once the lip 34 is placed against the cartilage surface 15, further stability could be provided to the guide 30 by axially advancing the tube 36 through the guide 30 such that the distal end 36*a* engages the acetabulum. It is also within the scope of this disclosure for the tube 36 to be located on the outer surface of the shaft 31, rather than being located within it. The tube 36 is made from a metal material. However, other material strong enough to withstand the forces placed on the tube 36 during repair may be used.

Figure 7:
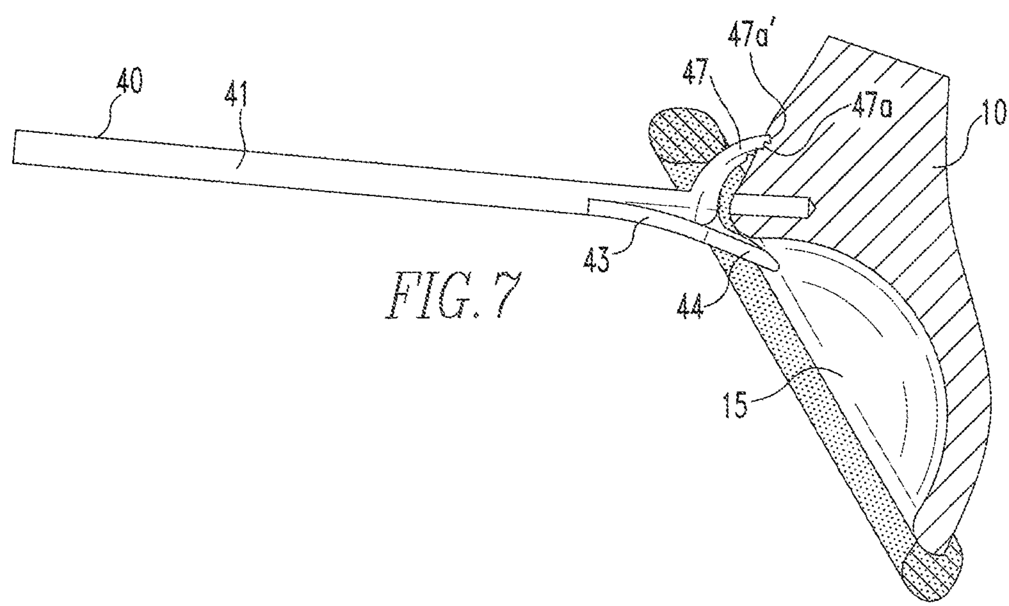
FIG. 7 shows a side view of a third guide of the present disclosure during use in acetabular labral repair.

FIG. 7 shows a third guide 40 for use in acetabular labral repair. The guide 40 is similar to guides 20, 30 except guide 40 includes a movable jaw 47 located at the distal end 43 of the shaft 41. The jaw 47 moves relative to the shaft 41 and the lip 44 and is used to engage the acetabulum 10, as will be further described below. The jaw 47 may be designed to fully close against the lip 44 when not in use. The jaw 47 may be moved via use of an actuator (not shown) that would extend along the length of the shaft 41 to connect the jaw 47 to a lever mechanism (not shown) located on the handle (not shown) or the shaft 41. Another type of means for moving the jaw 47 known to one of skill in the art may be used. During use, once the lip 44 is placed against the cartilage surface 15, further stability could be provided to the guide 40 by engaging the jaw 47 with the acetabulum 10, as shown in FIG. 7. The bottom portion 47*a* of the jaw 47 may include features, such as teeth 47*a*', or other features, that would engage the acetabulum 10 and further stabilize the guide 40.

Additionally, it is within the scope of this disclosure that the jaw 47 could be locked in position once it has engaged the acetabulum 10 via use of a locking mechanism known to one of skill in the art. The locking mechanism would work in cooperation with the above-described actuator and lever to lock the jaw 47 in position. This may allow the user to remove his or her hand from the guide 40 during subsequent delivery of the anchor into the acetabulum 10. The jaw 47 includes a metal material, but may be made from another material strong enough to withstand the forces placed on the jaw 47 during use.

Figure 8:
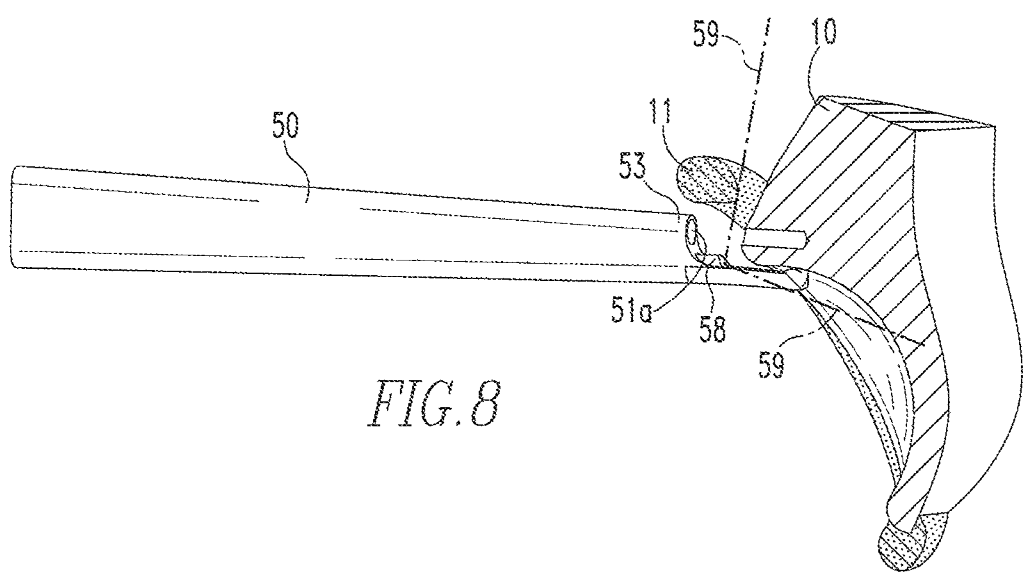
FIG. 8 shows a side view of a fourth guide of the present disclosure during use in acetabular labral repair.

FIG. 8 shows a fourth guide 50 for use in acetabular labral repair. The guide 50 is similar to guide 20 except guide 50 includes an arthroscope or endoscope 58. The arthroscope 58 is located within the guide 50 and may extend an entire length of the guide 50. As shown in FIG. 8, a portion of the scope 58 extends from the distal end 53 of the guide 50. However, it is within the scope of this disclosure that the arthroscope 58 wouldn't extend from the distal end 53 of the guide 50. Additionally, it is within the scope of this disclosure for the arthroscope 58 to be located within the guide 50, but above the cannulation 51*a* rather than below it. Furthermore, the arthroscope 58 may be located on the outer surface of the guide 50, rather than within it. A camera (not shown) may be coupled to the arthroscope 58 for processing of the image of the surgical area taken by the arthroscope 58. The camera may be coupled to a control unit (not shown) for further processing of the image prior to it being placed on a monitor (not shown) for viewing by the user. The field of view 59 of the arthroscope 58 would provide the additional benefit of direct visualization of the acetabulum/labrum 10/11 and especially the area of needed repair, thus substantially reducing the possibility of the above drawbacks of little or no visualization during repair.

While the guides 20, 30, 40, 50 are disclosed for being used in labral repair of the hip joint, it is within the scope of this disclosure that the guides 20, 30, 40, 50 could be used in labral repair of the shoulder joint or any other type of tissue repair.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A method of tissue repair of a hip joint, the hip joint having an acetabulum and a socket defined by the acetabulum, the socket having a surface and acetabular cartilage on the surface of the socket, the method comprising:

providing a guide, the guide comprising:

a handle;

a shaft including a proximal end coupled to the handle, a distal end, and a longitudinal axis extending between the proximal end and the distal end;

a lip branching from the shaft, wherein at least a portion of the lip is offset a distance from the longitudinal axis of the shaft, the lip having a distal contoured portion introducing the guide into the hip joint;

urging the distal contoured portion of the lip into contact with the acetabular cartilage on the surface of the socket;

delivering an anchor into the acetabulum via use of the guide; and using the anchor to reattach a labrum of the hip joint to the acetabulum.

2. The method of claim 1 wherein the lip extends from the distal end of the shaft.

3. The method of claim 1 wherein the shaft and the handle are cannulated.

4. The method of claim 1 wherein the method further comprises creating a hole in the acetabulum via use of the guide.

5. The method of claim 1 wherein the offset distance is about 1 Mill to about 5 mm.

6. The method of claim 1 further comprising steps of:

urging the distal end of the shaft into position with respect to the labrum and engaging with the acetabulum via the distal end of the shaft.

7. The method of claim 6 wherein engaging with the acetabulum via the distal end includes penetrating the acetabulum in line with the longitudinal axis.

8. The method of claim 1 wherein the lip extends distally a distance from the distal end of the shaft.

9. The method of claim 1 wherein the distal contoured portion of the lip includes a surface contoured along the longitudinal axis to substantially match a curvature of the articular cartilage on the surface of the socket.

10. The method of claim 9 wherein the distance the lip extends distally from the end of the shaft is about 13 mm to about 25 mm.

11. The method of claim 1, wherein the distal contoured portion of the lip includes a surface having a convex curvature along the longitudinal axis.

12. The method of claim 11, wherein the convex curvature substantially matches a concave curvature of the articular cartilage on the surface of the socket.

13. The method of claim 11, wherein the surface having the convex curvature also has a concave curvature along the longitudinal access, the concave curvature being proximal relative to the convex curvature.

14. The method of claim 13, wherein the surface of the distal contoured portion defines a smooth transition between the concave and convex curvatures.

15. The method of claim 1, wherein the distal contoured portion of the lip includes a surface having a concave curvature along the longitudinal axis.

16. The method of claim 15, wherein the concave curvature substantially matches a convex curvature of the articular cartilage around the rim of the socket.

* * * * *